United States Patent

Kappey et al.

[11] Patent Number: 6,114,301
[45] Date of Patent: Sep. 5, 2000

[54] 2,4,6-TRIMETHYL-4-PHENYL-1,3-DIOXANE

[75] Inventors: Claus-Hermann Kappey, Holzminden; Bernd Hölscher, Halle; Wilhelm Pickenhagen, Höxter, all of Germany

[73] Assignee: Dragoco Gerberding & Co. KG, Germany

[21] Appl. No.: 09/306,543

[22] Filed: May 6, 1999

[30] Foreign Application Priority Data

May 7, 1998 [DE] Germany .......... 198 22 232

[51] Int. Cl.⁷ .............. A61K 7/02; A61K 7/40; A61K 47/30; A61K 7/32; C07D 319/06
[52] U.S. Cl. .............. 512/12; 549/369; 514/844; 514/772; 512/25; 424/65; 424/76.1; 424/76.4
[58] Field of Search .............. 549/369; 424/65, 424/76.1, 76.4; 514/844, 772; 512/12, 25

[56] References Cited

FOREIGN PATENT DOCUMENTS 62-205200   9/1987   Japan .
9629281     9/1996   WIPO .
9806804     2/1998   WIPO .

*Primary Examiner*—Alan L. Rotman
*Assistant Examiner*—Rita Desai
*Attorney, Agent, or Firm*—Pendorf & Cutliff

[57] ABSTRACT

There is described a compound of general formula (2RS, 4SR,6X)-2,4,6-Rimethyl-4-phenyl-1,3-dioxane with the configuration characteristic X=RS (Compound 1) or SR

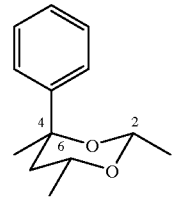

(d, I)

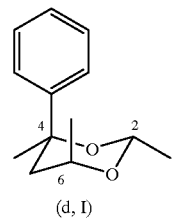

(d, I)

The compounds 1 and 3 possess a fragrance which can be described as strong, herbal-fresh, green, typically grapefruit.

Further described are new processes for production of a mixture of the compounds (2RS,4SR,6RS)-2,4,6-trimethyl-4-phenyl-1,3-dioxane (1) and (2RS,4RS,6RS)-2,4,6-trimethyl-4-phenyl-1,3-dioxane (2).

4 Claims, No Drawings

2,4,6-TRIMETHYL-4-PHENYL-1,3-DIOXANE

BACKGROUND OF THE INVENTION

1. Field of the Invention

The present invention concerns 2,4,6-trimethyl-4-phenyl-1,3-dioxane of the general Formula C.

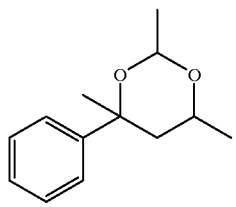

C

2. Description of the Related Art

In the fragrance industry, there is a constant need for new aromatic substances. The employment of 2,4,6-trimethyl-4-phenyl-1,3-dioxane of the general Formula C in fragrance mixtures is already known and is referenced in patent documents WO 9629281 (The Procter & Gamble Company, USA), JP 62205200 (Kao Corp., Japan), and JP 60014859 (Ogawa and Co., Ltd., Japan). Information regarding the isomer forms of the 1,3-dioxane C, or as the case may be, the specific sensory characteristics, are not to be found in these documents.

In the Chemical Abstracts (Chem. Abs. Vol. 64, 11217f [1966]), there is reference to a patent of the Sanyo Chemical Industry Co. (of K. Uno et al., Japan. 102 ('66), January 7, Appl. Nov. 28, 1962) which concerns the production of 1,3-dioxanes from aliphatic aldehydes with olefins under alumina catalysis. As an example, the conversion of two molar equivalents of paraldehyde (corresponding to six mole equivalents of acetaldehyde) to 2,4,4,6-tetramethyl-1,3-dioxane is carried out with three mole equivalents isobutene in the presence of acidic alumina. It is indicated that in a similar manner 2,4,6-trimethyl-4-phenyl-3-dioxane of general Formula C can be produced, which to the person of ordinary skill in this art means that the 1,3-dioxane of general Formula C was synthesized from the corresponding amounts of α-methylstyrol (A) and paraldehyde (B) in the presence of acidic alumina.

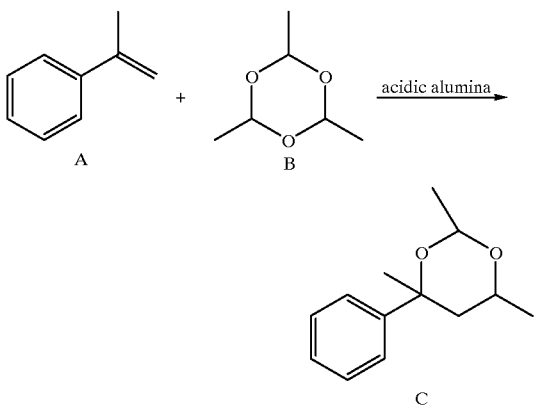

R. El Gharbi et al. (Synthesis 1971, 361–2; Tetrahedron Vol. 39, 2953–63 [1983]) describe mixtures of two isomeric forms (diasteriomeric enantiomer pairs 1 and 2) of 2,4,6-trimethyl-4-phenyl-1,3-dioxane. The isomers (2RS,4SR, 6RS)-2,4,6-trimethyl-4-phenyl-1,3-dioxane (1) and (2RS,4RS,6RS)-2,4,6-trimethyl-4-phenyl-1,3-dioxane (2) are formed in easily distinguishable relationship by condensation of alpha-methylstyrol (A) with two mole equivalents of acetaldehyde under catalysis of strongly acidic cationic exchange resins (Lewatit® SP 120, Bayer AG) depending upon solvents and reaction time and temperature. For the conversion in toluol at 20° C., there is reported after twenty-four hours a relationship of 1/2 of 68:32; for the conversion in hexane at 20° C. after one hour, or as the case may be at 50° C. after 0.5 hours, there is reported a relationship 1/2 of 62:38, or as the case may be, 65:35. The person of skill in this art would easily conclude therefrom that under the above-described reaction conditions the thermodynamic equilibrium, for example, during the conversion in toluol after 24 hours, was achieved with the 68:32 relationship of substances 1 and 2.

R. el Gharbi et al. observed that the condensation of an alkene with aliphatic and aromatic aldehydes—with the exception of formaldehydes—in the presence of sulfuric acids generally leads to a complex product mixture (glycols, dimers, crotonization of the aldehydes, polymers, etc.), so that this catalyst appears to be unsuitable for achievement of good yields of the corresponding substituted 1,3-dioxanes.

Information or data regarding the sensory properties of 1 and 2, or as the case may be the mixtures thereof, are not included in the two above-described publications.

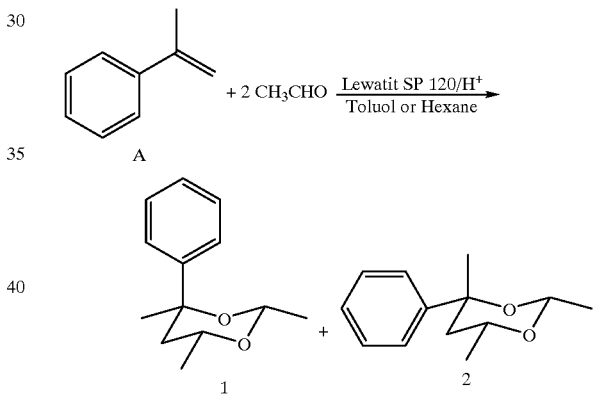

A mixture of isomers 2,4,6-trimethyl-4-phenyl-1,3-dioxanes, which contains as main components the isomers 1 and 2, has been employed for more than twenty years as an aromatic substance and sold under the names VERTACETAL (manufacturer: Dragoco Gerberding & Co. AG, Holzminden) and FLOROPAL/CORPS 717 (manufacturer: Haarmann & Reimer GmbH, Holzminden).

The two commercial products differ—as has now been determined by in-house analysis—with respect to their content in the main components 1 and 2, but differences have now also been determined with respect to the content of the now identified, respectively present minor constituents (2RS,4SR,6SR)-2,4,6-trimethyl-4-phenyl-1,3-dioxane (3) and (2SR,4SR,6RS)-2,4,6-trimethyl-4-phenyl-1,3-dioxane (4) as well as the minor components 3,6-dihydro-cis-2,6-dimethyl-4-phenyl-2H-pyran (5) and 3,6-dihydro-trans-2,6-dimethyl-4-phenyl-2H-pyran (6) (compare this to the below "comparative analysis"). The compounds 3, 4, and 6 were previously not known, they are described in greater detail below and spectroscopically analyzed in the context of the Examples.

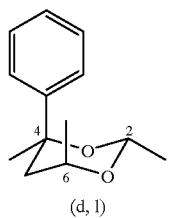

(d,l)

3

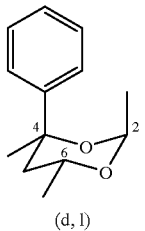

(d,l)

4

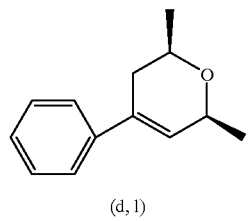

(d,l)

5

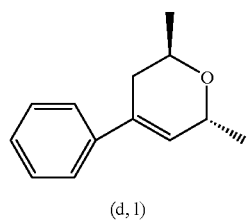

(d,l)

6

In the corresponding product specification sheets, the aroma of VERTACETAL is described as "fresh-herbal, typically the impression of grapefruit", and the aroma of FLOROPAL/CORPS 717 is described as "herbal-fresh, floral-green similar to chrysanthemum, cyprus, and grapefruit." A respective individualized sensory description of the two main components 1 and 2 as well as the minor components 3, 4, 5, and 6 has not previously been available.

SUMMARY OF THE INVENTION

The present invention was premised on the task of providing an aromatic substance, which with respect to its aromatic characteristic corresponds at least approximately to the known mixtures of isomers of 2,4,6-trimethyl-4-phenyl-1,3-dioxanes, but which as much as possible is more intensive than this.

This task is achieved by specifying the compounds (2RS,4SR,6RS)-2,4,6-trimethyl-4-phenyl-1,3-dioxane (1) and (2RS,4SR,6SR)-2,4,6-trimethyl-4-phenyl-1,3-dioxane (3) as Aromatic Substances

DETAILED DESCRIPTION OF THE INVENTION

The invention is concerned first on the surprising discovery that of the known mixed isomers 2,4,6-trimethyl-4-phenyl-1,3-dioxanes, (2RS,4SR,6RS)-2,4,6-trimethyl-4-phenyl-1,3-dioxane (1) acts as active aroma substance while the other main component 2 in mixture with component 1 can have even a detracting influence upon the sensory properties and thus during an employment in the perfume art can have a disadvantageous effect (for comparison, see the following Example 5). From the series of minor components 3, 4, 5, and 6, it is surprising that the compound 3, the (2RS,4SR,6SR)-2,4,6-trimethyl-4-phenyl-1,3-dioxane, has aromatic properties; it's fragrance characteristics correspond substantially to that of 1.

As aromatic substance, it is advantageous to employ the pure (2RS,4SR,6RS)-2,4,6-trimethyl-4-phenyl-1,3-dioxane (1), which can be isolated for example by distillation from a mixture of substances 1 and 2. In comparison to the until now known (commercially available) aromatic substance mixtures, the employment of the new aromatic substance mixture is already advantageous when it contains an increased proportion of (2RS,4SR,6RS)-2,4,6-trimethyl-4-phenyl-1,3-dioxane (1). This type of aromatic substance mixture with a component of (2RS,4SR,6RS)-2,4,6-trimethyl-4-phenyl-1,3-dioxane (1) of preferably greater than 80 weight percent or a preferred proportional relationship of substances 1 and 2 of at least 4:1 can be prepared, for example, by a distillative further processing of the aromatic substance mixtures produced in the conventional industrial manner.

The advantages resulting from employment of the pure compound 1 or of mixtures with the increased proportion of 1 are in particularly evident from a comparison of the aroma threshold values of compounds 1 and 2 determined by the triangle test.

| Aromatic threshold values: | |
|---|---|
| Compound 1 | 0.85 μ/l water |
| Compound 2 | 332 μ/l water |

The employment of (2Rs,4SR,6RS)-2,4,6-trimethyl-4-phenyl-1,3-dioxane (1) or highly concentrated mixtures with the substance 1 as main component results in a reduction of transport and storage costs by dispensing with or, as the case may be, reducing the proportion of sensorially inactive or disadvantageous ballast-components.

In the framework of the invention, a series of new aspects have developed also with respect to the manufacturing process.

So it was surprisingly found, that a good yield of a mixture of substances 1 and 2 (besides small amounts of secondary components) with a preferred proportional relationship of 1 to 2$\geq$80:20 directly from α-methylstyrol and paraldehyde or acetaldehyde under catalytic influence of Brönsted-acids, preferably aqueous sulfuric acid, can be synthesized without there being any concern of the general formation of a complex product mixture under the influence of sulfuric acid. As alternative catalyst, there can also advantageously be employed diluted other strong Brönsted acids, such as, for example, perchloric acid, acid salts, phosphoric acid, or p-toluolsulphonic acid. In an advantageous embodiment for production of the mixture of compounds (2RS,4SR,6RS)-2,4,6-trimethyl-4-phenyl-1,3-dioxane (1) and (2RS,4RS,6RS)-2,4,6-trimethyl-4-phenyl-1,3-dioxane (2) there are thus converted α-methylstyrol and paraldehyde or acetaldehyde under the influence of Brönsted-acids, preferably aqueous sulfuric acid at 20–30° C. (compare Example 3 further below).

According to a further inventive process for production of (2RS,4SR,6RS)-2,4,6-trimethyl-4-phenyl-1,3-dioxane (1) a (for example commercially available) mixture of compounds 1 and 2 (with minor components or by products) are treated in acid, preferably with a Brönsted-acid at 20–30° C. The compound 2 (and equal amounts of minor component 3 and 4) is thereby at least partially converted into compound 1. As catalyst, sulfuric acid is preferred, there can, however, also be employed other strong Brönsted-acids, such as for example perchloric acid, acid salts, phosphoric acid, or p-toluenesulphonic acid. As Lewis-acids, there can be employed, for example bor(III)fluoride, aluminum chloride, zinc chloride, or titanium(IV)chloride can be employed as catalysts. This inventive process leads surprisingly also to mixtures with a heightened or increased proportion of substance 1; the relationship of substances 1 and 2 correspond in a typical case to 84:16, relationships of at least 84:20 can regularly be achieved (compare below Example 4, Alternative a).

In an alternative inventive process for production of (2RS,4SR,6RS)-2,4,6-trimethyl-4-phenyl-1,3-dioxane (1) (2RS,4RS,6RS)-2,4,6-trimethyl-4-phenyl-1,3-dioxane (2) is used as starting material and preferably treated with an acid (compare below Example 4, Alternative b). Here, likewise, a conversion or transformation occurs, which results in a mixture with an increased component of substance 1. The end product (2RS,4RS,6RS)-2,4,6-trimethyl-4-phenyl-1,3-dioxane (2) can be separated out for example by a distillation of the mixture of substances 1 and 2.

In the following, the invention will be described in greater detail on the basis of a comparative analysis of commercially available products and on the basis of inventive examples:

Comparative Analysis

Analysis of Conventional Mixtures with a Proportion of (2RS,4SR,6RS)-2,4,6-trimethyl-4-phenyl-1,3-dioxane (1)

For characterizing conventional products, two sample mixtures of different origin (see Table) were analyzed gas chromatographically using a 60 m-glass capillary column (DBWax, 50–200° C.,4° C./min):

$t_R$=30.0 (1), 31.75 (3), 31.8 (4), 33.75 (2), 35.2 (5), 36.7 min (6).

The classification occurred per GC/MS-Analysis by correlation with a pure component, for example, an 11:1 mixture of 3/4.

TABLE 1

Observed distribution (surface area percentage) of compounds 1–6:

| Commercially available/Compound | 1 | 2 | 3 | 4 | 5 | 6 |
|---|---|---|---|---|---|---|
| VERTACETAL (Dragoco Gerberding & Co. AG) | 54.38 | 44.33 | 1.06 | 0.10 | 0.13 | — |
| FLOROPAL/CORPS 717 (Haarmann & Reimer GmbH) | 63.71 | 34.52 | 0.76 | 0.17 | 0.80 | 0.04 |

EXAMPLE 1

Distillative Separation of (2RS,4SR,6RS)-2,4,6-trimethyl-4-phenyl-1,3-dioxane (1)

3500 g VERTACETAL (commercial product of Dragoco Gerberding & Co. AG, GC-Analysis—see the preceding comparative analysis, Table 1) were fractionally distilled using a 1.5 m—metal packing column (BX-Packing, Co. Sulzer) at a pressure of 9–9.5 hPa.

(a) In the boiling point range 99–101° C. 1868 g (2RS, 4SR,6RS)-2,4,6-trimethyl-4-phenyl-1,3-dioxane were distilled as colorless fluid; GC-purity: 99.9%.

The following data resulted for (2RS,4SR,6RS)-2,4,6-trimethyl-4-phenyl-1,3-dioxane (1):

Odor: strong, herbal-fresh, green, typical grapefruit.

$^1$H-NMR (300 MH$_z$, CDCL$_8$): δ=1.21 (d, J=6.5 Hz, 3 H), 1.33 (d, J=5 Hz, 3 H), 1.40 (s, 3 H), 1.67 (dd, J=11.5 Hz, J=14 Hz, 1 H), 2.32 (dd, J=2 Hz, J=14 Hz, 1H), 3.65 (ddq (12 lines), J=2 Hz, J=11.5 Hz, J=6.5 Hz, 1 H), 4.70 (q, J=5 Hz, 1 H), 7.19–7.26 (m, 1 H), 7.31–7.37 ppm (m, 4 H).

$^{13}$C-NMR (75 MH$_z$ CDCL$_8$): δ=21.1 (q), 21.6 (q), 34.3 (q), 41.0 (t), 68.9 (d), 76.4 (s), 93.6 (d), 125.8 (d), 126.8 (d), 128.6 (d), 144.4 ppm (s).

MS: m/z (%)–206 (Track, M$^+$), 191 (10), 147 (16), 146 (51), 145 (53), 131 (61), 121 (14), 118 (24), 117 (21), 105 (100), 103 (11), 91 (21), 77 (30), 51 (11), 45 (18), 43 (60)

(b) In the boiling point range 101–106° C., there were distilled 128.5 g of distillate as colorless fluid which, according to the gas chromatogram (60 m DBWax, 50–200° C., 4° C./min) contained 25.8% 1, 28.9% 3, 2.7% 4 and 42.6% 2. From the above described material, an analytic sample of 3/4 in a relationship 11:1 was isolated by means of preparative gas chromatography.

The result was the following—surprising with respect to the aroma—analysis results for (2RS,4SR,6SR)-2,4,6-trimethyl-4-phenyl-1,3-dioxane (3).

Aroma: Strong, verbal-fresh, green, typical grapefruit (determined by GC-Sniffing-Analysis). [Observation: The new substance (2RS,4SR,6SR)-2,4,6-trimethyl-4-phenyl-1, 3-dioxane (3) is thus an excellent aromatic substance.)

$^1$H-NMR (300 MH$_z$, CDCL$_3$): δ=1.15 (d, J=6.5 H$_z$, 3 H), 1.37 (d, J=5 H$_z$, 3 H), 1.48 (s, 3 H), 2.16 (dd [B-part of an AB-Spectrum]), J=8 H$_z$, J=14 H$_z$, 1 H) 2.19 (dd [A-part of an AB Spectrum]), J=5 H$_z$, J=14 H$_z$, 1H), 4.26 (ddq [14 lines]), J=5 H$_z$, J=8 H$_z$, J=14 H$_z$, 1H), 5.01 (q, J=5 H$_z$, 1H), 7.22–7.29 (m, 1 H), 7.33–7.38 ppm (m, 4 H).

MS: m/z (%)=191 (19, M$^+$–15), 147 (13), 146 (29), 145 (46), 131 (29), 118 (17), 117 (17), 105 (100), 91 (18), 77 (21), 45 (15), 43 (38).

Besides this, the following analytical results were produced for (2SR,4SR,6RS)-2,4,6-trimethyl-4-phenyl-1,3-dioxane (4).

Aroma: Not noticeable (determined by GC-Sniffing-Analysis).

$^1$H-NMR (300 MH$_z$, CDCL$_3$: as far as can be determined in mixture with 3):=1.40 (d, J=5 H$_z$, 3 H), 1.56 (s, 3 H), 3.72–3.85 (m, 1 H), 5.41 ppm (q, J=5 H$_z$, 1 H).

MS: m/z (%)=191 (19, M$^+$–15), 162 (36), 147 (17), 145 (51), 121 (17), 118 (11), 117 (14), 106 (11), 105 (100), 103 (11), 91 (16), 77 (26), 51 (10), 45 (14), 43 (36).

(c) In the boiling point range 106–108° C., there was obtained 1105 g 2 as colorless fluid; GC-purity 99.9%. At the conclusion of the distillation, 324 g bottom product remained as weakly yellow fluid, which, according to gas chromatogram contained 98.43% 2, 1.41% 5 and 0.07% 6.

The following analytical results were produced for (2RS, 4RS,6RS)-2,4,6-trimethyl-4-phenyl-1,3-dioxane (2).

Aroma: a very weak, like chemical solvent.

$^1$H-NMR (300 MH$_z$, CDCL$_8$): δ=1.22 (d, J=6 H$_z$, 3 H), 1.41 (d, J=5 H$_z$, 3 H), 1.58 (s, 3 H), 1.60 (dd, J=11.5 H$_z$, J=13

$H_z$, 1 H), 1.79 (dd, J+2.5 $H_z$, J=13 $H_z$, 1 H), 4.00 (ddq [12 lines], J=2.5 $H_z$, J=11.5 $H_z$, J=6 $H_z$, 1 H), 5.18 (q, J=5 $H_z$, 1H), 7.18–7.25 (m, 1H), 7.29–7.37 (m, 2 H), 7.42–7.46 ppm (m, 2 H).

$^{13C}$-NMR (75 $MH_z$, $CDCL_8$): δ=21.6 (q), 21.8 (q), 23.2 (q), 43.6 (t), 68.5 (d), 74.5 (s), 92.2 (d), 123.9 (d), 126.6 (d), 128.1 (d), 148.9 ppm (s).

MS: m/z (5)=206 (0.2, M$^+$), 191 (42), 162 (24), 147 (14), 145 (26), 121 (19), 118 (11), 117 (12), 106 (10), 105 (100), 91 (11), 77 (24), 45 (15), 43 (35).

EXAMPLE 2

Production of a Mixture of Substances 1 and 2 with Use of a Strong Acidic Ionic Exchange Resin To a well stirred suspension of 5 g Amberlyst® 15 (dry, manufactured by Aldrich) in 100 g toluol and 1.5 g water, there were drop wise added at 20° C., with occasional ice water cooling, in 1 hour a mixture of 118 g (1 mol) α-methylstyrol (A) and 88 g (2 mol) acetaldehyde. The reaction mixture was stirred at room temperature overnight. Filtering off the catalyst, the solvent was distilled off in 20 mbar vacuum. The distillation of the residue (189.5 g) in a 30 cm—metal packing column in 9 hpa-vacuum produced 153.7 g substance mixture 1/2 (74.6% d.Th.) in boiling point range 100–108° C. as colorless fluid, which as determined by gas chromatogram (30 mDBWax, 100–240° C., 6° C./min) was comprised of the following composition: 54.2% 1, 0.4% 3/4, 45.2% 2, 0.2% 5.

EXAMPLE 3

The Production of a Mixture of Substances 1 and 2 with an Increased Proportion of Substance 1 from α-methylstyrol (A) and Paraldehyde (B) Under Influence of Acquiesce Sulfuric Acid To a well stirred two-phase mixture of 183 g hexane-fraction (boiling point range 63–80° C.) and 250 g of an acid mixture of 210 g formic acid, 12.5 g sulfuric acid (96 wt. %) and 27.5 g water, there was at 20–25° C., with occasional ice water cooling, drop-wise added in 1 hour a mixture of 223 g (1.89 mol) α-methylstyrol (A) and 183 g (1,385 mol) paraldehyde (B). The reaction mixture was stirred a total of 30 hours at 25° C. The acidic phase was separated off, and the organic phase was washed twice with 100 g water and once with 125 g 5 wt. % soda solution. After distilling off the solvent at normal pressure, there remained 395 g raw material, which according to the gas chromatogram (30 m DBWAX, 100–240° C., 6° C./min) exhibited the following compositional makeup: 82.0% 1, 0.5% 3/4, 15.8% 2, 1.6% 5, 0.1% 6.

(For comparison: an analytical sample, which was removed after 20 h stirring and was worked up as discussed above, exhibited the following gas chromatographic distribution: 80.5% 1, 0.5% 3/4, 17.7% 2, 1.3% 5).

The distillation of the raw product in a 40 cm-metal packing column produced 341.9 g of a mixture of substances 1 and 2 (87.8% d.Th.) in the boiling point range 100–108° C./9 hPa as colorless fluid, which according to the gas chromatogram contained 83.4% 1, 0.5% 3/4 and 16.1% 2. This product mixture exhibited, in comparison to the commercially available mixtures VERTACETAL and FLOROPAL/CORPS 717, (compare the above comparative analysis) as more intense odor and a more pleasant smell.

Further, 10.3 g were subsequently obtained in the boiling point range 108–111° C./9 hPa as yellow fluid, which according to the gas chromatogram contained 1.3% 1, 1.8% 3/4, 46.7% 2, 46.1% 5, and 2.7% 6. From this obtained material, there were isolated by means of preparative gas chromatographic analysis amounts of the pure dihydropropane 5 and 6.

There resulted the following analytic results for 3,6-dihydro-cis-2,6-dimethyl-4-phenyl-2H-pyran (5).

Aroma: Not significant (determined per GC-sniffing-analysis)

$^1$H-NMR (300 $MH_z$, $CDCL_3$): δ1.33 (d, J=7 $H_z$, 3 H), 1.36 (d, J=6 $H_z$, 3H), 2.32–2.36 (m, 2 H), 3.81 (sextet, J=6 $H_z$, 1 H), 4.40 (m, 1 H), 6.01 (q, J=1.5 $H_z$, 1H), 7.23–7.43 ppm (m, 5 H).

$^{13}$C-NMR (75 $MH_z$, $CDCL_3$): δ=21.6 (q), 21.7 (q), 34.6 (t) 70.2 (d), 71.3 (d), 124.8 (d), 127.2 (2 d), 128.4 (d), 134.2 (s), 140.2 ppm (s).

MS: m/z (%)=188 (69, M$^+$), 173 (39), 159 (53), 145 (91), 131 (78), 130 (41), 129 (54), 128 (41), 117 (27), 115 (30), 103 (26), 91 (35), 43 (100).

And, finally, there resulted the following analytical results for 3,6-dihydro-trans-2,6-dimethyl-4-phenyl-2H-pyran (6):

Aroma: Very weak, chemical-technical (determined by GC-Sniffing-Analysis).

$^1$H-NMR (300 $MH_z$, $CDCL_3$): δ=1.32 (d, J =6 $H_z$, 3 H), 1.33 (d, J=7 $H_z$, 3 H), 2.25 (ddt, J=2.5 $H_z$, J=8.5 $H_z$, J=16.5 $H_z$, 1 H), 2.43 (ddt. J=1 $H_z$, J=3.5 $H_z$, J=16.5 $H_z$, 1 H), 4.00 (m, 1 H), 4.55 (m, 1 H), 6.06 (m, 1 H), 7.22–7.40 ppm (m, 5 H).

MS: m/z (%)=188 (66, M$^+$), 173 (49), 159 (55), 145 (90), 131 (77), 130 (39), 129 (56), 128 (43), 115 (29), 103 (32), 91 (35), 43 (100).

EXAMPLE 4

Production of Mixtures of (2RS,4SR,6RS)-2,4,6-trimethyl-4-phenyl-1,3-dioxane (1) and (2RS,4RS,6RS)-2,4,6-trimethyl-4-phenyl-1,3-dioxane (2) with an Increased Proportion of Isomer 1

Alternative a:

Production of a Mixture of Substances 1 and 2 with an Isomer Relationship 1/2=1.2 with Employment of Bor(III)fluoride ethyletherate 25 g of the mixture 1/2 according to Example 2 were dissolved in 25 g absolute $CH_2Cl_2$ and at 20° C. in a nitrogen atmosphere were converted with stirring with 0.5 g bor(III) fluoride-ethyletherate. The reaction mixture which turned a deep, dark yellow was stirred at room temperature for 7 hours. Then the reaction mixture was washed to neutral with 5 wt. % soda solution, and under normal pressure, freed of solvent. After ball tube distillation of the remaining residue (24.3 g) in 3 hPa-vacuum one obtained 23.4 g of product as colorless fluid, which according to gas chromatogram contained 72.5% 1, 4.5% 4-phenylbutane-2-one, 0.5% 3/4, 12.6% 2, 8.5% 5, and 1.2% 6.

Alternative b:

Production from (2RS,4RS,6RS)-2,4,6-trimethyl-4-phenyl-1,3-dioxane (2) Under the Influence of Acquiesce Sulfuric Acid A solution of 250 g 2 (from Example 1; GC-purity: 99.9%) in 250 g hexane-fraction (boiling point range 63–80°

C.) was converted under intensive stirring of 250 g of a acid mixture of 220 g formic acid, 2.5 g sulfuric acid (96 weight percent) and 27.5 g water in 10 minutes at 20° C. and subsequently stirred overnight (15 hours) at room temperature. The two phase system was worked up analogously to Example 3. There remained 248 g raw product, which according to gas chromatogram (30 m DBWAX, 100–240° C., 6° C./min) exhibited the following composition:

80.5% 1, 0.6% 3/4, 15.0% 2, 3.7% 5, 0.2% 6.

The distillation of the raw product in a 40 cm—metal packing column produced 233.3 g 1/2 (93.3% d.Th.) in boiling point range 100–108° C./9 hPa as colorless fluid, which according to the gas chromatogram contained:

83.8% 1, 0.6% 3/4, and 15.6% 2.

EXAMPLE 5

Test Series: Variations of a perfume oil from citrus-type/sensory effects of the presence of substance 1 and/or 2 in various concentrations and concentration relationships.

Addition of a fixed amount 1+2 with variable proportions of 1 and 2.

TABLE 2

| Perfume oil components | Perfume Oil Mixtures | | | | | |
|---|---|---|---|---|---|---|
| | a | b | c | d | e | f |
| Thiocineol 1% | 10 | 10 | 10 | 10 | 10 | 10 |
| Oxane* 10% | 2 | 2 | 2 | 2 | 2 | 2 |
| Cis-3-Hexenol 10% | 5 | 5 | 5 | 5 | 5 | 5 |
| Hivertal 10% | 10 | 10 | 10 | 10 | 10 | 10 |
| Aldehyde C10 | 10 | 10 | 10 | 10 | 10 | 10 |
| Aldehyde C12 | 5 | 5 | 5 | 5 | 5 | 5 |
| Dihydromyrcenol | 50 | 50 | 50 | 50 | 50 | 50 |
| Geranylnitrile | 10 | 10 | 10 | 10 | 10 | 10 |
| Orange oil Brazilian | 200 | 200 | 200 | 200 | 200 | 200 |
| Citrus oil Italian | 360 | 360 | 360 | 360 | 360 | 360 |
| Citral | 100 | 100 | 100 | 100 | 100 | 100 |
| Terpinols 20 | 108 | 108 | 108 | 108 | 108 | 108 |
| Litsea Cubebail dist. | 100 | 100 | 100 | 100 | 100 | 100 |
| Allylcapronate | 10 | 10 | 10 | 10 | 10 | 10 |
| Isomer 2 (pure) | — | 30 | — | — | — | — |
| Mixture 1 / 2 (55:45) | — | — | 30 | — | — | — |
| Mixture 1 / 2 (65:35) | — | — | — | 30 | — | — |
| Mixture 1 / 2 (80:20) | — | — | — | — | 30 | — |
| Isomer 1 (pure) | — | — | — | — | — | 30 |

*Product of Company Firmenich (Trade Name)

The mixture a produced a citrus-based mixture. It contained neither (2RS,4SR,6RS)-2,4,6-trimethyl-4-phenyl-1,3-dioxane (1) nor (2RS,4RS,6RS)-2,4,6-trimethyl-4-phenyl-1,3-dioxane (2).

Mixture b contained, in comparison with mixture a, additionally 3% of the substance 2. The mixture b smelled slightly less intense than the base mixture a.

In the alternative presence of 3% of a 55:45-mixture 1/2 (mixture c) or as the case may be of 3% of a 65:35 mixture 1/2 (mixture d) the perfume oil gains with increasing concentration of 1 and increase in freshness and naturalness in comparison to the flatter acting mixtures a and b.

In alternative presence of 3% of a 80:20 mixture 1/2 (mixture e) or as the case may be 3% of a pure substance 1 (mixture f), this positive effect occurred in an increasing manner, which exceeded the effect of the mere concentration increase of 1 and which was experienced as an over proportional increased natural emanation from mixtures e and f in comparison to the mixtures c and d, which were noticeably less green and peel-like in aroma.

EXAMPLE 6

Test Series: Variations of a perfume oil of citrus-type/sensory effecting the presence of substance 2 in various concentrations beside equally constituted concentrations of substance 1

Addition of a fixed amount 1 and variable amounts of 2 according to the following:

TABLE 3

| Perfume oil components | Perfume Oil Mixtures | | | | |
|---|---|---|---|---|---|
| | a | g | h | i | f |
| Thiocineol 1% | 10 | 10 | 10 | 10 | 10 |
| Oxane* 10% ig | 2 | 2 | 2 | 2 | 2 |
| Cis-3-Hexenol 10% | 5 | 5 | 5 | 5 | 5 |
| Hivertal 10% | 10 | 10 | 10 | 10 | 10 |
| Aldehyde C10 | 10 | 10 | 10 | 10 | 10 |
| Aldehyde C12 | 5 | 5 | 5 | 5 | 5 |
| Dihydromyrcenol | 50 | 50 | 50 | 50 | 50 |
| Geranylnitrile | 10 | 10 | 10 | 10 | 10 |
| Orange oil Brazilian | 200 | 200 | 200 | 200 | 200 |
| Citrus oil Italian | 350 | 350 | 350 | 350 | 350 |
| Citral | 100 | 100 | 100 | 100 | 100 |
| Terpinols 20 | 108 | 108 | 108 | 108 | 108 |
| Litsea Cubebail dist. | 100 | 100 | 100 | 100 | 100 |
| Allylcapronate | 10 | 10 | 10 | 10 | 10 |
| Mixture 1 / 2 (55:50) | — | 60 | — | — | — |
| Mixture 1 / 2 (60:40) | — | — | 50 | — | — |
| Mixture 1 / 2 (80:20) | — | — | — | 37.5 | — |
| Isomer 1 (pure) | — | — | — | — | 30 |

*Product of Company Firmenich (Trade Name)

The mixture a is the citrus-based mixture, which was also employed in the test series according to Example 5; the mixture f was likewise already employed in this test series.

The mixtures g, h, i, and f contain respectively 30 parts of substance 1 and varying proportions of substance 2. Each of the mixtures g, h, i, and f, in comparison with the base mixture a, smells fresher and more natural.

In comparison of mixtures g, h, i, and f, with each other, there is to be noticed with a decreasing concentration of substance 2 (from g via h and i towards f) a significant, advantageous strengthening of the natural green peel aroma, whereby at the same time in the series progression g, h, i, and f, the emission and balance of the perfume increases in a desired manner.

EXAMPLE 7

Perfume Oils (Feminine Note), according to the following:

TABLE 4

| | a | b |
|---|---|---|
| Helional | 15 | 15 |
| Heliotropin | 5 | 5 |
| Hydroxycitronellal | 40 | 40 |
| Methyliridone gamma | 200 | 200 |
| Phenylethylalcohol | 100 | 100 |
| Base Jasmine 231* | 15 | 15 |
| Base Rose de Mai* | 15 | 15 |
| Hedione[c]** | 40 | 40 |
| Lilial[c]*** | 15 | 15 |
| Lyral[c]**** | 60 | 60 |
| Patchoulioil Indonesian rectified | 60 | 60 |
| Habanolide[c]** | 60 | 60 |
| Exaltolide[c]** | 30 | 30 |
| Linalool | 20 | 20 |
| Undecalactione -gamma | 20 | 20 |

TABLE 4-continued

| | a | b |
|---|---|---|
| Eugenol | 10 | 10 |
| Geraniol | 10 | 10 |
| Hexylacetate | 10 | 10 |
| Methyloctincarbonate 1% | 10 | 10 |
| Vanillin | 10 | 10 |
| Allylcyclohexanpropionate 10% | 5 | 5 |
| Anethole | 5 | 5 |
| Cassis Bourgeons absolute essence 1% | 5 | 5 |
| Cedar leaf oil 10% | 5 | 5 |
| Cis-3-hexanylacetate 10% | 5 | 5 |
| Citronella oil | 5 | 5 |
| Cumarin | 5 | 5 |
| Dimethylbenzylcarbinylacetate | 5 | 5 |
| Ethylcaprylate 10% | 5 | 5 |
| Isoeugenylacetate | 5 | 5 |
| Phenyldimethylcarbinol | 5 | 5 |
| Styraxoil 10% | 5 | 5 |
| Violet leaf absolute essence 10% | 5 | 5 |
| Iris absolute 10% | 2 | 2 |
| Wine yeast oil green 10% | 5 | 5 |
| Ylang-Oil | 5 | 5 |
| Cassis 345** 10% ig | 3 | 3 |
| Rosenoxide-L* 10% ig | 3 | 3 |
| Damascon-alpha** | 2 | 2 |
| Decalactone-gamma | 2 | 2 |
| Ethylvanillin | 2 | 2 |
| Evernyl[c]*** | 2 | 2 |
| Ethylcapronate 10% ig | 3 | 3 |
| Isoamylacetate 10% ig | 2 | 2 |
| Jasmine absolute essence | 5 | 5 |
| Rose absolute essence Marocco | 2 | 2 |
| Rose Oil Bulgarian | 2 | 2 |
| Dipropylenglycol | 150 | 130 |
| Isomer 1 / 2 (according to Example 3) | — | 20 |

*Dragoco-Product (Trade name)
**Firmenich-Product (Trade name)
***Givaudan-Product (Trade name)
****IFF-Product (Trade name)

The mixture a produces a perfume oil variation of the type Yvresse (previously known as "Champagne"). It possesses a fruity, anise-like headnote with green elements, a floral central part with carnation aspects and a powdery, woody foundation with musk and oak moss character. The substitution or exchange of 2% dipropylenglycol in mixture a against 2% of the substance mixture 1/2 according to Example 3 results in mixture b. In comparison, mixture b in comparison to a is characterized by in its smell by a light, tangy, fruity note. The aroma evolution of b has an overall finer balance and in after-smell b, in comparison with a, is more radiant and substantive.

EXAMPLE 8

Perfume Oil (Masculine Note) for EAU SAUVAGE according to the following:

TABLE 5

| | a | b |
|---|---|---|
| Hexylcinamaldehyde, alpha | 20 | 20 |
| Helional | 15 | 15 |
| Aldehyde C8 | 5 | 5 |
| Aldehyde C10 | 5 | 5 |
| Aldehyde C12 | 3 | 3 |
| Bergamot oil special* | 120 | 120 |
| Bergamot oil Reggio | 60 | 60 |
| Bergamot oil Italian | 40 | 40 |
| Analine** 10% | 2 | 2 |
| Linalool | 70 | 70 |
| Linalylacetate | 60 | 60 |
| Evernyl[c]** | 30 | 30 |
| Oak moss extract green Yugoslavian | 10 | 10 |
| Citral | 40 | 40 |
| Citrus oil Italian pelatrice | 30 | 30 |
| Lavandin oil Abrialis | 30 | 30 |
| Lavendel oil French | 20 | 20 |
| Orange oil Guinea | 15 | 15 |
| Limette oil distilled | 10 | 10 |
| Hedione[c]*** | 20 | 20 |
| Methyliridone gamma | 20 | 20 |
| Patchouli oil Indonesian rectified | 20 | 20 |
| Rose wood oil Brazilian | 20 | 20 |
| [2'S-(2'a,4'a ,8'a )]-Hexahydro-1',1',5',5'-tetramethylspiro [1,3-dioxolan-2,8'(5'H)-[2H-2,4a]methanonaphthalin]* | 15 | 15 |
| Base Amber* | 15 | 15 |
| Basil oil Comoren | 15 | 15 |
| Coriander oil | 15 | 15 |
| Carnation oil rectified | 10 | 10 |
| Rosmary oil tunesisch | 10 | 10 |
| Cumarin | 15 | 15 |
| Eugen oil | 15 | 15 |
| Base Jasmine 231* | 10 | 10 |
| Benzylacetate | 10 | 10 |
| Diheptylacetate* | 10 | 10 |
| Litsea Cubeba oil distilled | 10 | 10 |
| Methylchavic oil | 10 | 10 |
| Myrten oil | 10 | 10 |
| Sandranol | 10 | 10 |
| Amylvinylcarbinylacetate 10% | 5 | 5 |
| Angelikawurzel oil 10% | 5 | 5 |
| Carvon-L | 5 | 5 |
| Cumin oil | 5 | 5 |
| Geraniol | 5 | 5 |
| Geranium oil Bourbon | 5 | 5 |
| Geranylacetate | 5 | 5 |
| Geranylnitrile 10% | 5 | 5 |
| Habanolide[c]*** | 5 | 5 |
| Iris absolute essence 10% | 5 | 5 |
| Nerylacetate | 5 | 5 |
| Opoponax-Extract | 5 | 5 |
| Opoponax oil 10% | 2 | 2 |
| Olibanum oil | 2 | 2 |
| Sandlewood oil East Indian | 2 | 2 |
| Petitgrain oil Paraguay | 5 | 5 |
| Roseoxide inactive high cis* 10% | 5 | 5 |
| Terpineol | 5 | 5 |
| Vanillin 10% | 5 | 5 |
| Vetiver oil | 5 | 5 |
| Vetiverylacetate | 5 | 5 |
| Cinnamon leaf oil | 5 | 5 |
| Citronella oil | 3 | 3 |
| Heliotropin | 3 | 3 |
| Crinkle Mint American rectified | 3 | 3 |
| Ocimen | 3 | 3 |
| Undecalactone -gamma | 3 | 3 |
| Allycyclohexanpropionate 10% | 2 | 2 |
| Bay oil 10% | 2 | 2 |
| Hexylmethylether | 2 | 2 |
| Indol | 2 | 2 |
| Menthol-L | 2 | 2 |
| Novorosan[c]* 10% | 2 | 2 |
| Oct-1-en-3-ol 10% | 2 | 2 |
| Dipropylenglycol | 25 | 5 |
| Isomer 1 / 2 (according to Example 3) | — | 20 |

*Dragoco-Product (Trade name)
**H&R Florasynth-Product (Trade name)
***Givaudan-Product (Trade name)
****Firmenich-Product (Trade name)

The mixture a provides, in a 10% alcoholic solution, a classical eau-sauvage variation. It possesses an agrum headnote, a floral middle part with rooty sidenotes, and a woody foundation with mossy and moss-like resonation. By substitution of 2% dipropylenglycol in mixture a against 2% of the substance mixture 1/2 according to Example 3, one produces mixture b. In comparing the 10% alcoholic solutions mixture b characterizes itself in comparison to a by a substantially fresher, positively elevated headnote paired with a fine gardenia note in the middle part. The evolution of the experience of fragrance of b acts overall lighter, clearer, and weightier, and in the lingering smell of b, there occurs in comparison to a a highly desirable, natural, soft emission in the foreground.

What is claimed is:

1. A cosmetic or detergent composition comprising (2RS,4SR,6RS)-2,4,6-trimethyl-4-phenyl-1,3-dioxane (1) and (2RS,4RS,6RS)-2,4,6-trimethyl-4-phenyl-1,3-dioxane (2), wherein the ratio of compound (1) to compound (2) is at least 4:1.

2. A fragrance composition comprising (2RS,4SR,6RS)-2,4,6-trimethyl-4-phenyl-1,3-dioxane (1) and (2Rs,4RS,6RS)-2,4,6-trimethyl-4-phenyl-1,3-dioxane (2), is wherein the ratio of compound (1) to compound (2) at least 4:1.

3. A fragrance composition as in claim 2, wherein said composition comprises at least 80 weight percent (2RS,4SR,6RS)-2,4,6-trimethyl-4-phenyl-1,3-dioxane (1).

4. A process for altering the olfactory properties of a cosmetic composition, said process comprising adding to said cosmetic composition an olfactory property altering amount of a composition comprising (2RS,4SR,6S)-2,4,6-trimethyl-4-phenyl-1,3-dioxane (1) and (2RS,4RS,6X)-2,4,6-trimethyl-4-phenyl-1,3-dioxane (2), wherein the ratio of compound (1) to compound (2) is at least 4:1.

* * * * *